(12) United States Patent
Stofel et al.

(10) Patent No.: US 10,837,908 B2
(45) Date of Patent: Nov. 17, 2020

(54) SPATIAL IMAGING OF SCALP CARE AGENTS

(71) Applicant: The Procter & Gamble Company, Cincinnati, OH (US)

(72) Inventors: Samuel Wolfe Stofel, West Chester, OH (US); J. Frank Nash, Jr., West Chester, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

(21) Appl. No.: 16/388,032

(22) Filed: Apr. 18, 2019

(65) Prior Publication Data

US 2019/0323965 A1 Oct. 24, 2019

Related U.S. Application Data

(60) Provisional application No. 62/660,445, filed on Apr. 20, 2018.

(51) Int. Cl.
*G01N 21/64* (2006.01)
*A61B 5/00* (2006.01)

(52) U.S. Cl.
CPC ..... *G01N 21/6456* (2013.01); *G01N 21/6486* (2013.01); *A61B 5/446* (2013.01)

(58) Field of Classification Search
CPC ..... A61B 5/446; A61B 5/0071; A61B 5/0077; G01N 21/6456; G01N 21/6486; G01N 21/6458
See application file for complete search history.

(56) References Cited

U.S. PATENT DOCUMENTS

| 4,096,240 A | * | 6/1978 | Mathur | A61K 8/35 424/47 |
| 5,723,112 A | * | 3/1998 | Bowser | A61K 8/891 424/70.13 |
| 2002/0086039 A1 | * | 7/2002 | Lee | C03C 3/097 424/401 |
| 2005/0151094 A1 | * | 7/2005 | Kitagawa | G02B 21/0032 250/458.1 |

(Continued)

FOREIGN PATENT DOCUMENTS

| DE | 202013004905 U1 | * | 12/2013 | ........... G06T 11/001 |
| DE | 202013004905 U1 | | 2/2014 | |
| WO | WO2018173073 A1 | | 9/2018 | |

OTHER PUBLICATIONS

World Health Organization: International Agency for Research on Cancer, "Exposure to Artificial UV Radiation and Skin Cancer", (2006), IARC Working Group Reports, vol. 1, pp. 61-62 (Year: 2006).*

(Continued)

*Primary Examiner* — Chih-Cheng Kao
(74) *Attorney, Agent, or Firm* — Linda M. Sivik

(57) ABSTRACT

The present invention is directed to a method for measuring scalp care agents on/in skin or other substrate comprising the following steps: selecting a location within the treated area on the skin or other substrate; irradiate treated area using an actinic radiation source; and measure a resulting fluorescent emission of the scalp care agent or a photoconverted scalp care agent using either the actinic radiation source or a second radiation source to excite the sample.

17 Claims, 8 Drawing Sheets

(56) References Cited

U.S. PATENT DOCUMENTS

| | | | |
|---|---|---|---|
| 2010/0139682 A1 | 6/2010 | Edgar | |
| 2013/0284195 A1* | 10/2013 | Murdock | A45D 44/00 132/200 |
| 2016/0077077 A1* | 3/2016 | Shi | C12Q 1/02 435/29 |
| 2017/0209033 A1* | 7/2017 | Yu | A61B 1/07 |
| 2018/0321139 A1* | 11/2018 | Helfmann | A61B 5/441 |

OTHER PUBLICATIONS

Amy M. Holmes et al: "Imaging the penetration and distribution of zinc and zinc species after topical application of zinc pyrithione to human skin", Toxicology and Applied Pharmacology, vol. 343, Mar. 1, 2018, pp. 40-47.

Chen Guoqiang et al.: "Sensitive and simultaneous quantification of zinc pyrithione and climbazole deposition from anti-dandruff shampoos onto human scalp", Journal of Chromatography B: Biomedical Sciences & Applications, Elsevier, Amsterdam, NL, vol. 1003, Sep. 11, 2015, pp. 22-26.

Javier Lopez Flores et al., "Determination of azoxystrobin residues in grapes, musts and wines with a multicommuted flow-through optosensor implemented with photochemically induced fluorescence", Science Direct, Analytica Chimica Acta 585 (2007) 185-191.

Natalie L. Garrett et al.: "Imaging microscopic distribution of antifungal agents in dandruff treatments with stimulated Raman scattering microscopy", Journal of Biomedical Optics, vol. 22, No. 6, Jun. 9, 2017, p. 066003.

PCT International Search Report and Written Opinion for PCT/US2019/028015 dated Jul. 11, 2019.

Yanara Jeria et al., "Photochemically induced fluorescence coupled to second-order multivariate calibration as analytical tool for determining imidacloprid in honeybees", Chemometrics and Intelligent Laboratory Systems 160 (2017) 1-7.

* cited by examiner

| Scalp Care Agent | Excitation - 470nm Emission - 560nm No UV | Excitation - 365nm Emission - 415nm Initial Actinic Radiation | Excitation - 365nm Emission - 415nm End of Actinic Radiation | Excitation - 470 Emission - 560nm Post UV |
|---|---|---|---|---|
| Zinc Pyrithione | | | | |
| Piroctone Olamine | | | | |
| Climbazole | | | | |

Fig. 1

SPATIAL IMAGING OF SCALP CARE AGENTS

FIELD OF THE INVENTION

The present invention is directed to a method of detecting scalp care agents by measuring auto-fluorescent characteristics of a scalp care agent and/or measuring resulting fluorescent emission of photo-converted scalp care agents.

BACKGROUND OF THE INVENTION

Zinc Pyrithione (ZPT) is used across numerous disciplines as an effective biocide. One specific example is its incorporation into shampoo treatments as a means to combat the proliferation of the scalp irritating fungus, malassezia, and thereby mitigate the creation of dandruff. Despite the use of ZPT as a dandruff treatment, there is a desire for further understanding of the mechanism of action of ZPT on the malassezia fungus. As an effort to further elucidate this mechanism, it would be advantageous to understand one of the potential variables at play; the spatial deposition of ZPT on the scalp as a result of a dandruff treatment. Before such research can take place, a reliable detection method to spatially resolve ZPT on the scalp is needed.

In pursuing a methodology that can detect the presence of ZPT against a scalp background, many methods are considered and found to be insufficient. Traditional tape stripping of treated stratum corneum as well as cyanoacrylate tape stripping require that the sample be removed from the in vivo donor. Removing ZPT from the extended biological system is seen as undesirable as the context of the dynamic scalp environment in which it is deposited may provide important clues to its mechanism of action. Fluorescence tagging is another method of consideration. While a feasible approach in an in vivo context, it would have the undesired side effect of changing the physiochemical properties of the ZPT and therefore its native interaction with the skin surface would be compromised. Infrared imaging and Stimulated Raman Scattering (SRS) microscopy is deemed insufficient due to its diffraction limited low resolution. With ZPT particles having a diameter of a few microns or less a technique with a greater resolution is required. Autoradiography and X-ray fluorescence are not pursued due to safety considerations for the subjects being measured. More conventional methodologies such as visible light microscopy and laser scanning are also pursued, but found to have insufficiently unique reflectance profiles or morphologies, respectively, to confidently separate ZPT from the scalp background or other deposited moieties. All methods considered, there is a need for developing a detection method that can be used safely, in vivo, and be selective for spatially resolving ZPT. Moreover, an all-in-one technique that could additionally be used to detect the deposition of other scalp care agents, such as Piroctone Olamine and Climbazole would be highly advantageous.

SUMMARY OF THE INVENTION

The present invention is directed to a method for measuring scalp care agents on/in skin or other substrate comprising the following steps: selecting a location within the treated area on the skin or other substrate; irradiate treated area using an actinic radiation source; and measure a resulting fluorescent emission of the scalp care agent or a photo-converted scalp care agent using either the actinic radiation source or a second radiation source to excite the sample.

BRIEF DESCRIPTION OF THE DRAWINGS

FIG. 1. Table with non-limiting example images of three scalp care agents and their subsequent responses to actinic radiation. Sc/Rc where Sc=(S−dark)×Mcorrect and Rc=(R−dark)×Xcorrect in which Mcorrect and Xcorrect are Emission and Excitation correction factors respectively.

DETAILED DESCRIPTION OF THE INVENTION

All measurements are understood to be made at ambient conditions, where "ambient conditions" means conditions at about 25° C., under about one atmosphere of pressure, and at about 50% relative humidity, unless otherwise designated. All numeric ranges are inclusive of narrower ranges; delineated upper and lower range limits are combinable to create further ranges not explicitly delineated.

The present invention can comprise, consist essentially of, or consist of, the essential components as well as optional components, features or elements described herein. As used herein, "consisting essentially of" means that the component may include additional features or steps, but only if the additional components or steps do not materially alter the basic and novel characteristics of the claimed methods.

In the present invention actinic radiation refers to the range of wavelengths that create a photochemical reaction when incident upon scalp care agents. The set of wavelengths that have been determined to create this photochemical reaction have an upper value of about 450 nm. The set of wavelengths may further be in a range of about 100 nm to about 450 nm, further in a range of about 280-nm to about 450 nm and further in a range of about 315 nm to about 450 nm.

In the present invention, non-limiting examples of a substrate include hair, skin, scalp, an artificial surrogate, tape strip or fabric.

Figure 2:
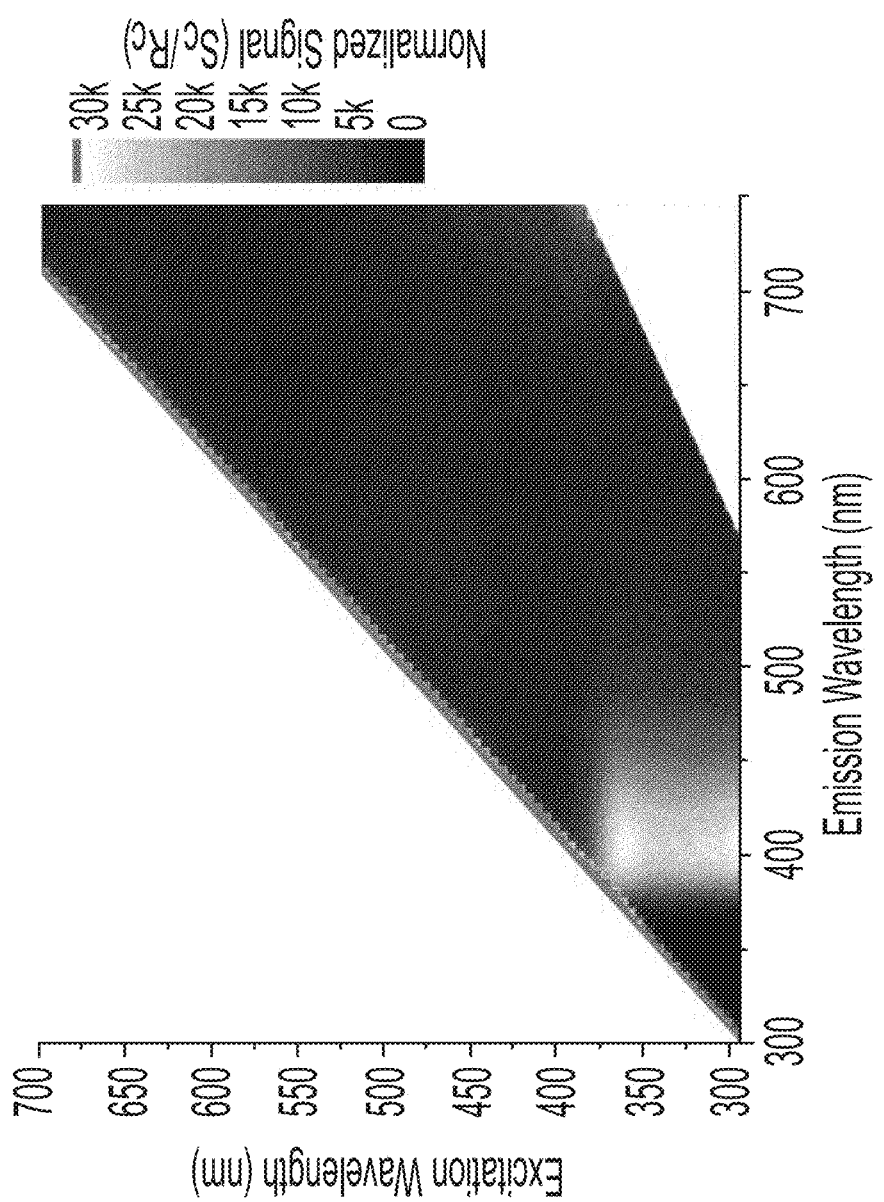
FIG. 2. Excitation Emission Matrix for ZPT Autofluorescence. Sigma Aldrich powder with 4.0 Neutral Density filter positioned in front of detector. Data above and below the $1^{st}$ and $2^{nd}$ order Raleigh scattering lines (respectively) have been masked out to reduce data complexity. When ZPT sample is irradiated with UV radiation, a fluorescent band is observed with a peak emission of 415 nm. Sc/Rc where Sc=(S−dark)×Mcorrect and Rc=(R−dark)×Xcorrect in which Mcorrect and Xcorrect are Emission and Excitation correction factors respectively.
Figure 3:
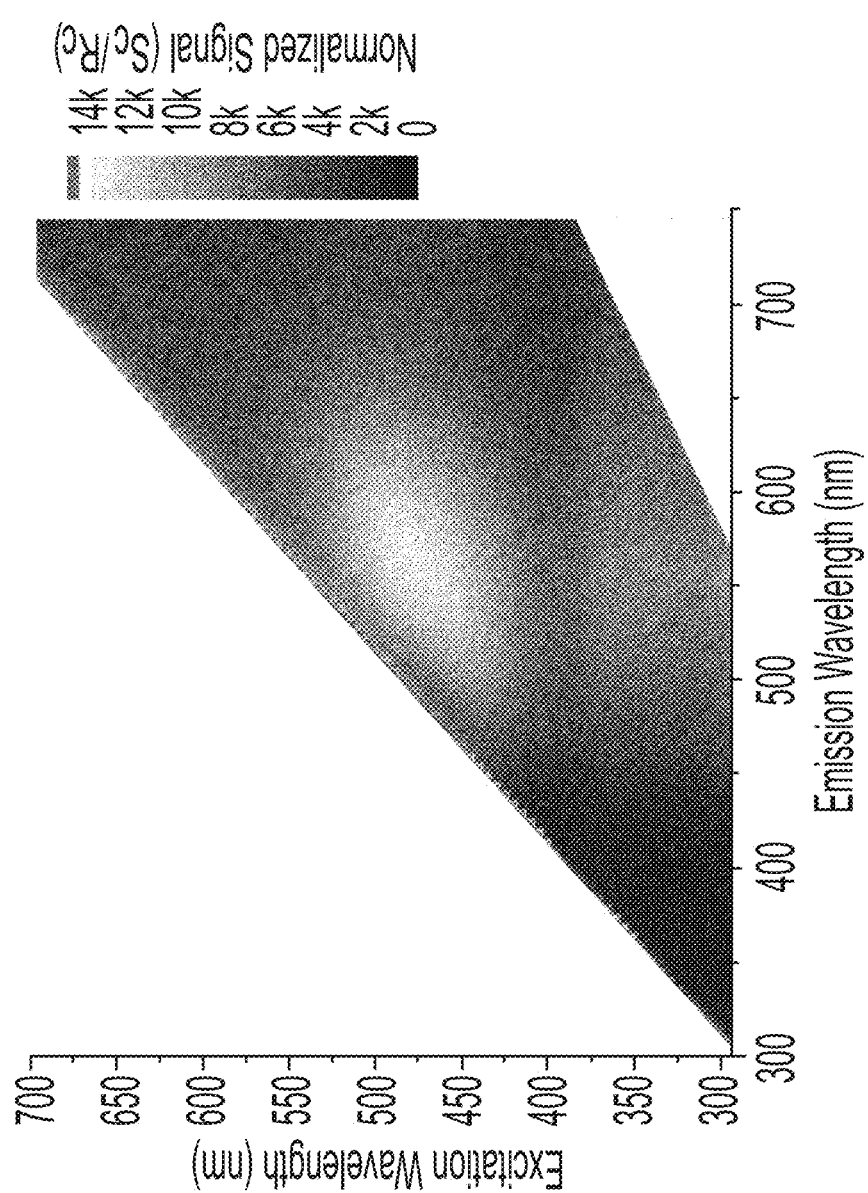
FIG. 3. Upon continued irradiation with UV radiation the auto fluorescence of ZPT diminishes to non-detectable levels and a new fluorescent signal, with a peak emission of between 550-570 nm, is detected and increased with exposure time.

In continuing to seek out a suitable technique, fluorescence is thoroughly investigated. Using a Jvon Hoben FluoroMax-4 Fluorometer, an excitation emission matrix (EEM) is developed to characterize ZPT auto fluorescence (See FIG. 1) and is found to have a peak emission of 410 nm when excited with UV radiation (peak efficiency at about 365 nm excitation). The present invention characterization of ZPT auto-fluorescence is the first of its kind. In attempting to leverage this newly identified fluorescent signal as a means to spatially locate ZPT, it is found to degrade rapidly with continued UV exposure suggesting a photochemical reaction is taking place. While it has been documented that ZPT is sensitive to UV radiation, the present invention has found that the progress of the reaction can be tracked using fluorescence. Additionally, the UV irradiated ZPT is observed to have changed in color from a bright white powder to one that is bright yellow-green. This observation prompts the creation of an EEM for the photo converted ZPT (hereinafter referred to as ZPT*). To ensure sufficient conversion of the ZPT had taken place, ZPT is placed in a Dymax ECE 2000 UV irradiation chamber for 1.5 hours. Post UV irradiation, the original auto-fluorescent ZPT signal falls below detectable levels and a new fluorescent emission is detected. The peak emission is measured to be between 550-570 nm, but there are two distinct peaks in excitation that are able to generate this new fluorescence signal with greater efficiency than others, namely about 365 nm and 470 nm (See FIG. 2).

As an effort to understand if both newly found and non-obvious fluorescent signals are unique to ZPT and ZPT*, EEM's are also generated for Zinc Carbonate and Scalp skin pre-and post UV irradiation. Zinc Carbonate, a potentiator of ZPT in some scalp care formulas, is found to have no appreciable autofluorescent signal neither before or after UV irradiation. Scalp skin does exhibit an appreciable autofluorescent signal with UV radiation; however, the autofluorescent signal decreases over time while the photoconverted ZPT exhibits an increasing fluorescent signal over time. This contrast in fluorescent behavior provides the ability to differentiate ZPT vs. scalp skin.

Methods

One manifestation of the present invention is a custom-built microscope to take advantage of the finding that ZPT is autofluorescent and can photo-convert from one fluorescent species to another in the presence of actinic radiation. The setup consists of two Excitation Arms (470 nm and 365 nm), 3 dichroic mirrors, a microscope objective, and two Emission Detector Arms (see FIG. 4 for setup). Each Emission Detector Arms consists of a camera, tube lens, and bandpass filter. Emission Detector Arm 1 contains a bandpass filter centered at 415 nm. Emission Detector Arm 2 contains a bandpass filter centered at 560 nm.

Figure 4:
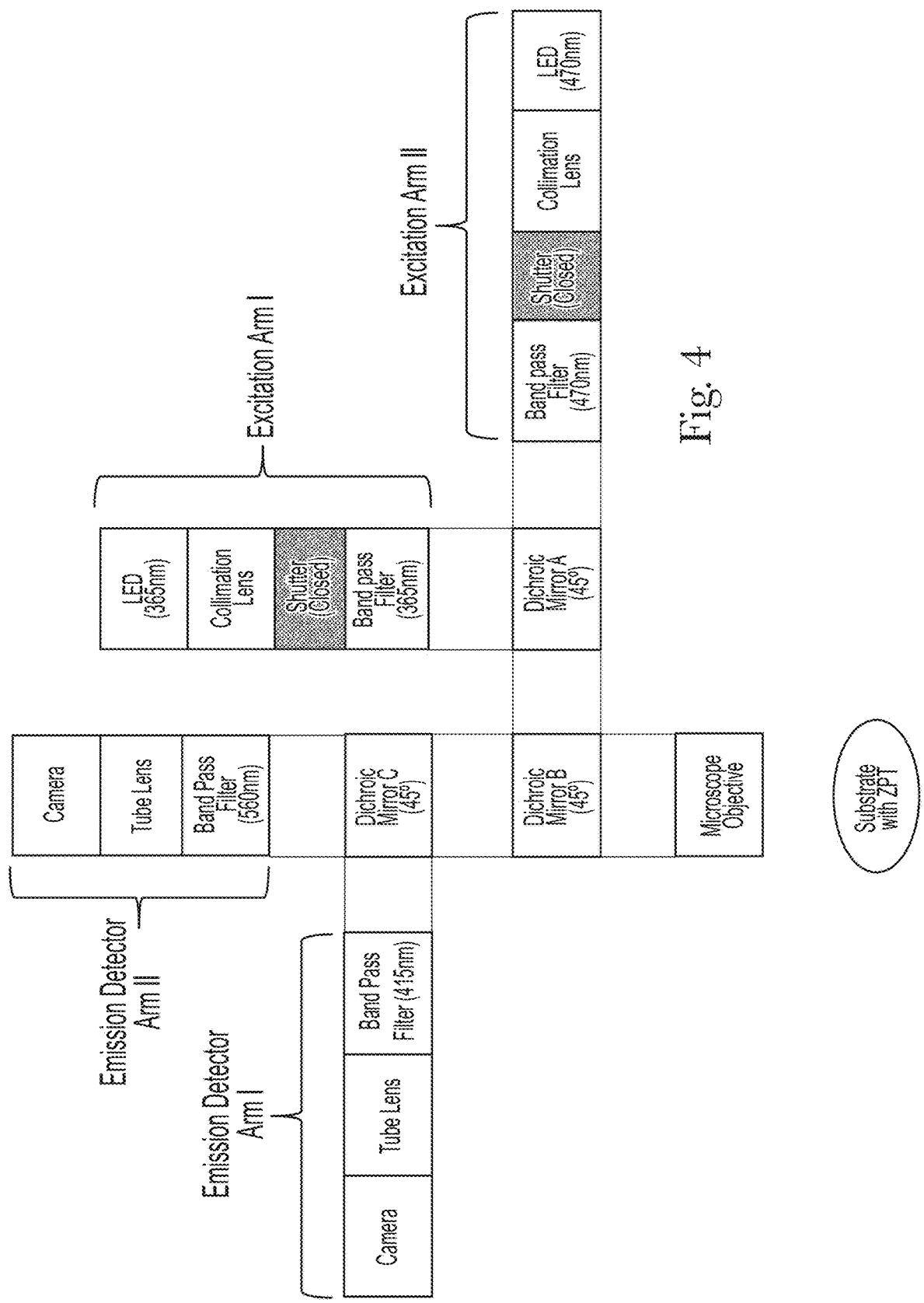
FIG. 4. Diagram depicting a non-limiting example of an instrument capable of detecting both the auto-fluorescence of ZPT as well as the red shifted fluorescence from photo-converted ZPT as a result of continued irradiation with UV radiation (365 nm).
Figure 5:
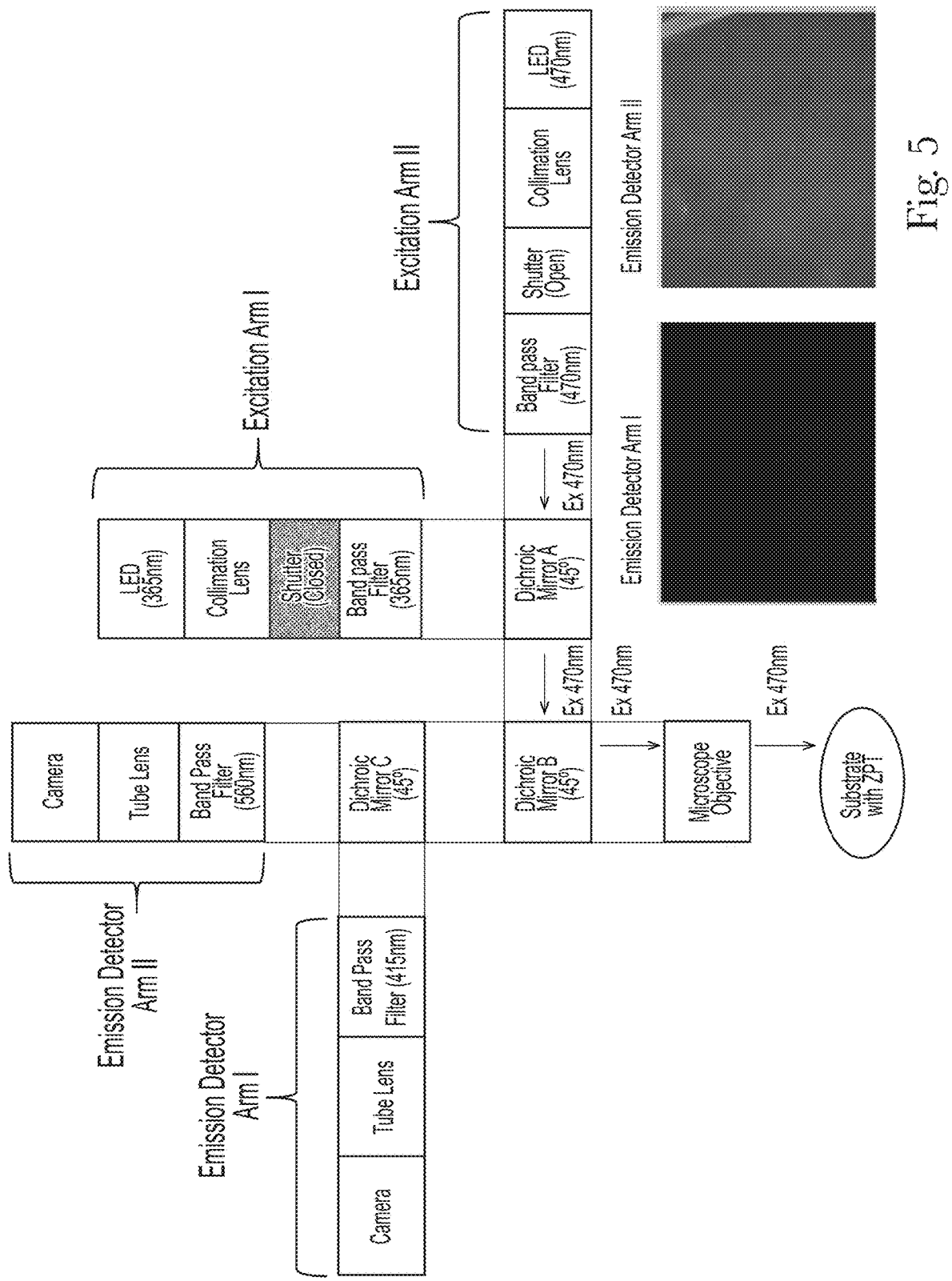
FIG. 5. Diagram and nonlimiting example images showing the light path of Excitation Arm II. It uses a light source that does not appreciably photo-convert ZPT, if at all, allowing the user to locate a suitable area for measurement and adjust focus as needed. During this phase of the measurement, Emission Detector Arm I will not receive any signal and Emission Detector Arm II detects mainly the auto fluorescence of skin.
Figure 6:
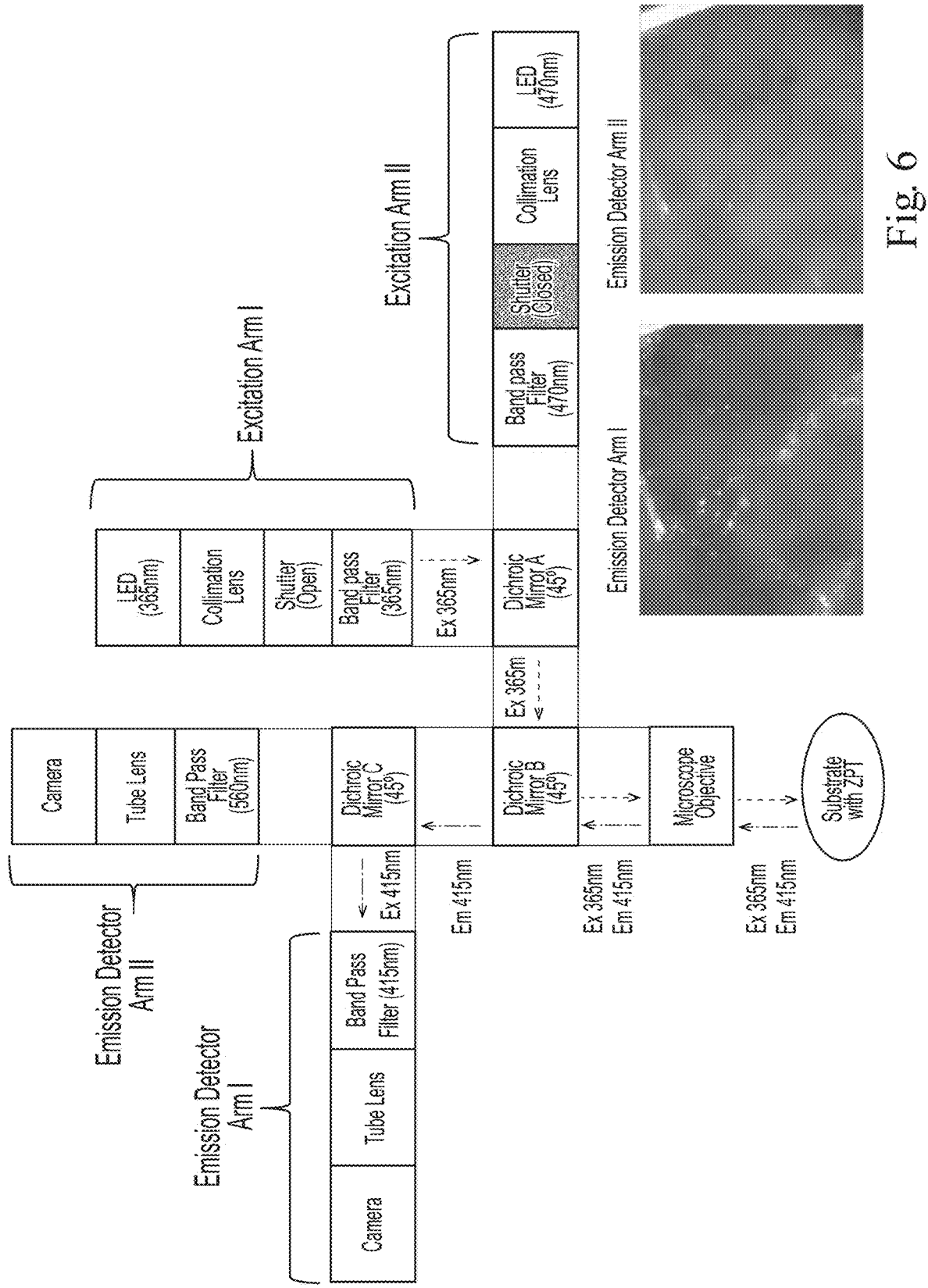
FIG. 6. Diagram and nonlimiting example images showing the path of radiation from Excitation Arm I resulting in the detection of the autofluorescent signal of ZPT using Emission Detector Arm I. Emssion Detector Arm II initially shows the autofluorescence of skin and minimal signal from ZPT.

For a typical measurement, the shutter for Excitation Arm I is initially closed and the shutter for Excitation Arm II is open to allow the light centered at 470 nm to interact with the sample (See FIG. 4 for light path). This illumination allows the user to locate a suitable area for measurement and ensure the microscope is appropriately focused prior to irradiating the sample with UV radiation. A suitable area may include a location within a treated area with a scalp care agent which provides for a sharp focus, with no hair fibers in the field of view and wherein such a location within a treated area may be less than 1 cm in diameter. Further, the location within a treated area may be in a range of about 2.5 microns to about 25 centimeters (cm) or from about 2.5 microns to about 2.5 cm. or from about 2.5 microns to about 2.5 millimeters (mm). Once the area of interest and focus have been established, the shutter in front of the 470 nm LED is closed and the shutter in front of the 365 nm LED is opened and exposed to an actinic radiation source (See FIG. 5 for radiation path). Upon interaction with the ZPT containing substrate, the ZPT will autofluoresce. This is an example wherein the actinic radiation source acts as a means to both photoconvert and excite the ZPT sample. The autofluorescence will have a peak emission of 415 nm in which an image is captured by Emission Detector Arm I. Simultaneously, an image is also captured by Emission Detector Arm II. ZPT will have little to no emission captured by Emission Detector Arm II, but this image may serve as a baseline for later subtraction. With continued irradiation with the 365 nm LED source, the ZPT will photo-convert to a hypothesized new chemical species, previously defined as ZPT*, that exhibits a red shift in fluorescence relative to native ZPT. This is an example wherein the actinic radiation source is used to excite the photoconverted ZPT sample. The autofluorescent ZPT signal detected by Emission Detector Arm I will fade over time to a small fraction of its original intensity. In contrast, the emission from ZPT* will increase with continued UV irradiation. After a period of time, both Emission Detector Arm I and II are triggered to capture their respective images (See FIG. 6 for radiation paths). The absolute difference between the baseline and post UV images are calculated for each of the two cameras. If the signal from the substrate does not change with UV exposure over time and the images have been appropriately registered then the absolute value images can be multiplied together to enhance the signal from ZPT and ZPT* to create a single image with an enhanced signal to noise ratio that identifies the location of ZPT/ZPT* in the sample. In practice, it has been found that the autofluorescence of many substrates will decrease over time with continued irradiation with 365 nm radiation. In these cases, absolute signal from ZPT* post UV vs. baseline alone has proven to yield satisfactory results. In cases where the baseline and post-UV images cannot be registered (i.e. too much movement during the UV irradiation), applying morphology filters to the autofluorescent ZPT or post UV ZPT* images has provided satisfactory results in detecting ZPT vs. the skin background.

Figure 7:
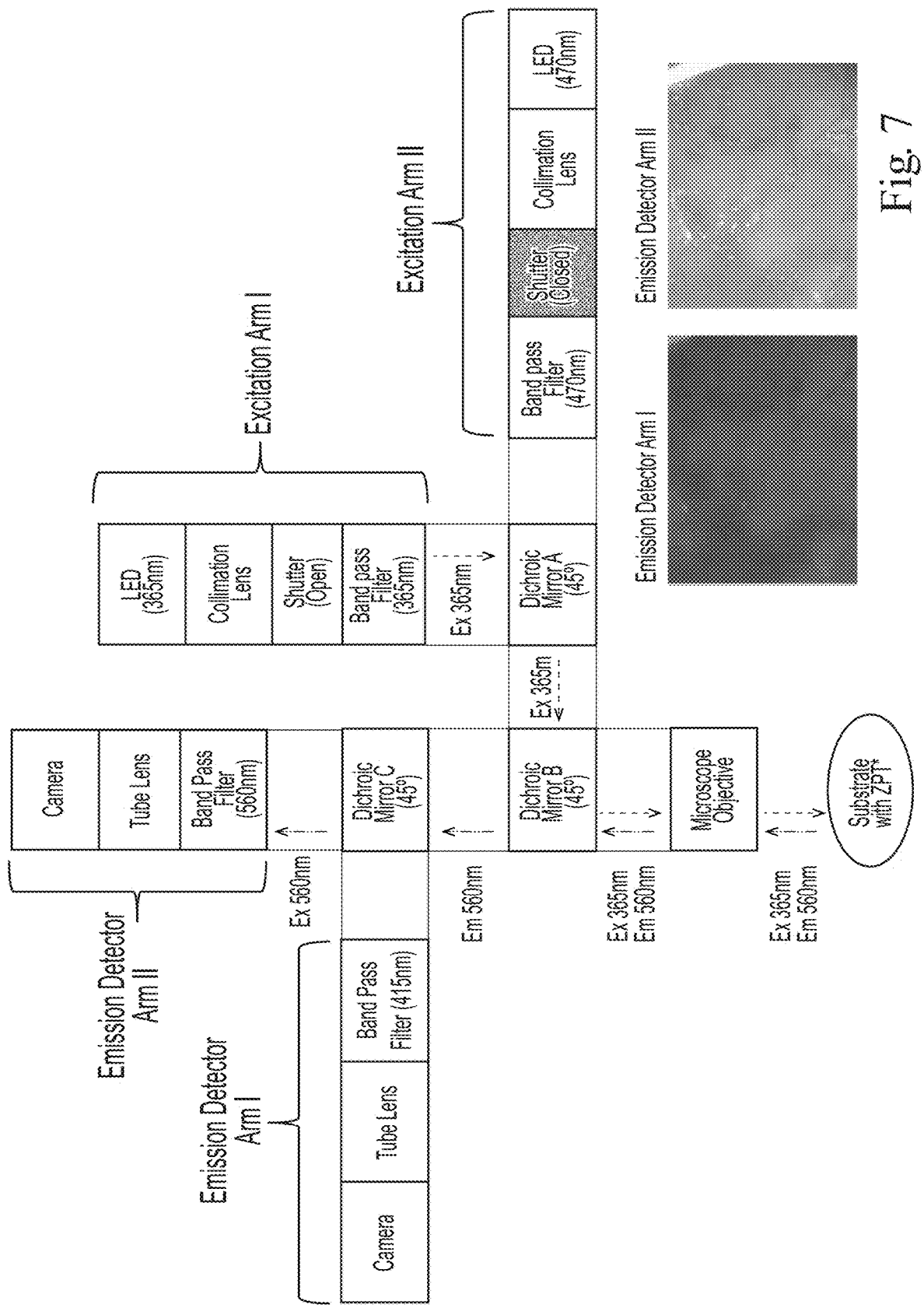
FIG. 7. Diagram and images showing a non-limiting example of the change in flourescence detected in Emission Detector Arm 1 and Emmission Detector Arm II with continued irradiation with the UV radiation. With continued irradiation, the autofluorescent ZPT signal detected by Emission Detector Arm I will fade to undetectable levels while that new fluorescent signal of ZPT* (photo converted ZPT) detected by Emission Detector Arm II will grow in intensity.
Figure 8:
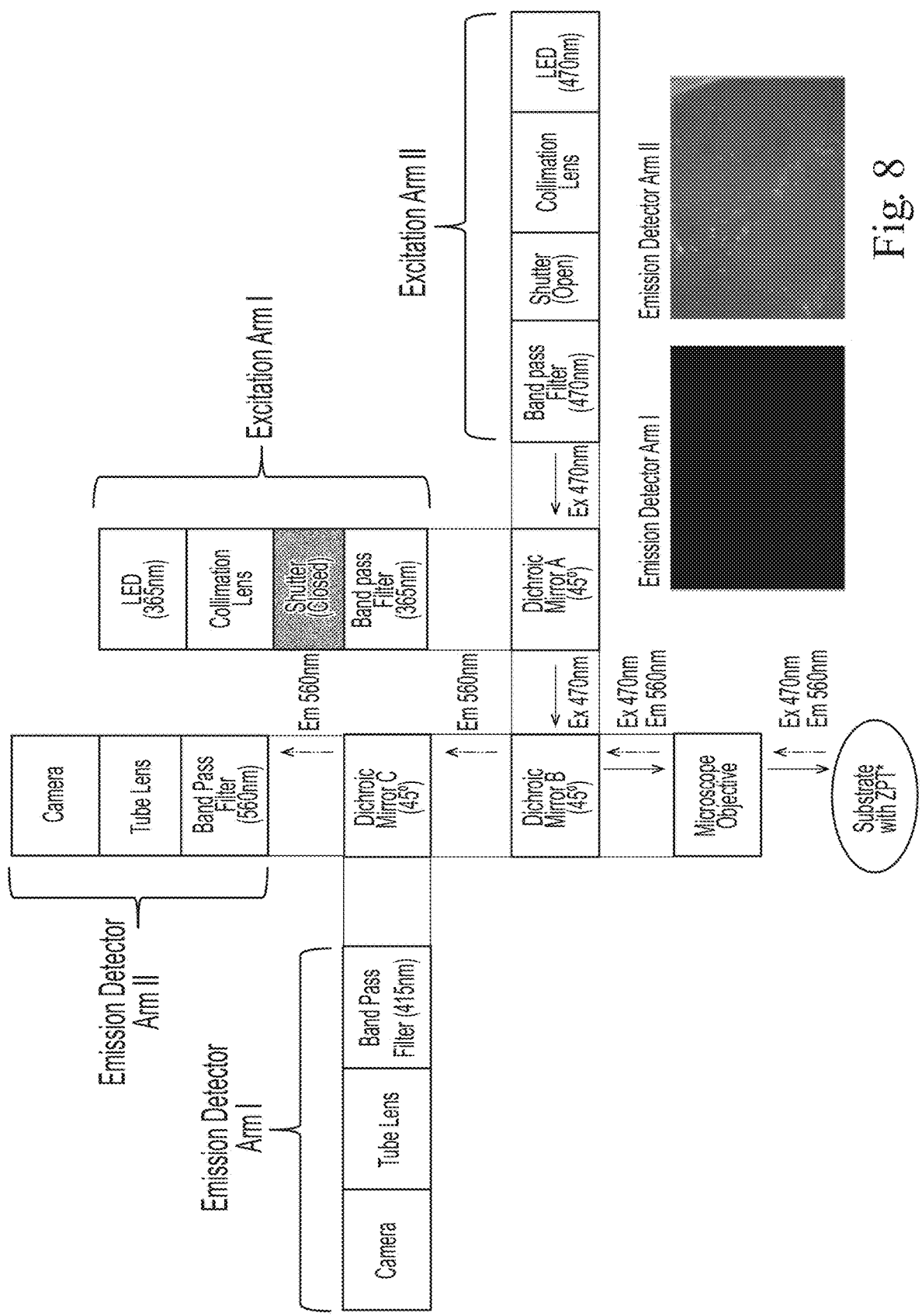
FIG. 8. Diagram and images showing a nonlimiting example of the path of radiation from Excitation Arm II after the ZPT has been photo-converted using UV radiation. Only Emission Detector Arm II will detect the new fluorescent signal of the photo-converted ZPT.

For long term observations post UV irradiation, the shutter for Excitation Arm I is closed and the shutter for Excitation Arm II is opened again allowing the user to continue to detect the fluorescence of ZPT* from Emission Detector Arm II (See FIG. 7 for light path). This is an example of wherein a second radiation source is used to excite the photoconverted ZPT and is different from the actinic radiation source.

Conceivably, the system can be further optimized with the appropriate bandpass filter and dichroic mirror to have only a single camera in which the radiation sources can be modulated in a manner that allows for the ZPT and ZPT* images to be captured in rapid succession.

Moreover, the system could be further enhanced by incorporating confocal capability. Another manifestation involves a non-spatially resolved imaging capability in which the overall autofluorescent signal of ZPT, change in autofluorescence of ZPT, or increase in fluorescence of ZPT* is measured upon irradiation with UV radiation. An example being an optical fiber assembly attached to a spectrophotometer. Further refinement could involve either UV or non-UV radiation sources, more broadly referred to as actinic radiation. It has been found that radiation wavelengths up to 450 nm has sufficient energy to photo-convert ZPT, albeit at a much slower rate, than higher frequency UV radiation.

Results/Data Section

In addition to ZPT, other scalp care agents are found to also exhibit a response to actinic radiation and a subsequent shift in fluorescence due to a hypothesized photo-chemical reaction. A non-limiting summary can be seen in FIG. 1 as an example of detectable shifts in fluorescence when actinic radiation is introduced. The examples provided include Zinc Pyrithione, Piroctone Olamine, and Climbazole. As described earlier and depicted in the first row of scalp care agents in FIG. 1, ZPT deposited on skin exhibits a relatively small level of autofluorescence when excited with 470 nm light. When initially excited with 365 nm radiation, a strong autofluorescence is evident. Images captured under the initial incidence of actinic radiation can be used for both qualitative and quantitative assessments of ZPT spatial deposition. Continued irradiation with UV will diminish ZPT's autofluorescent signal to a fraction of its initial strength. Images with this diminished signal can be subtracted from the images showcasing the initial autofluorescence under actinic radiation to create a more accurate quantifiable image with the skin background removed. Finally, removing the UV radiation and re-exciting the sample with 470 nm light will show a new fluorescent signal that is not present prior to the actinic irradiation. Images with the new fluorescent signal can be used for both qualitative and quantitative assessments. Furthermore, subtracting the initial image captured under 470 nm light can be used to remove the background creating a more accurate image of where ZPT, or it's photo-converted species, is located.

The second scalp care agent depicted in a non-limiting example in FIG. 1, Piroctone Olamine, is placed in a shampoo formulation and then diluted 1 part shampoo to 10 parts distilled water. The sample is then shaken in a 2 oz vial for 30 seconds and the resulting lather is spread onto a microscope slide. Once dry, the following sequence of images in row 2 of FIG. 1 are captured. Initially, the Piroctone Olamine in the shampoo exhibits relatively small levels of autofluorescence when excited with 470 nm light. Upon actinic irradiation, the initial autofluorescence is also relatively low; however, a shift in the fluorescent signal reveals the location of Piroctone Olamine, or its photo-converted species, readily. This is a non-limiting example wherein the radiation source used to excite the sample is the actinic radiation source. Removing UV irradiation and re-exciting Piroctone Olamine with 470 nm light (a second radiation source) shows an increase of fluorescence that gradually fades with continued irradiation. It appears that Piroctone Olamine has recrystallized into solid particles.

The final scalp care agent depicted in FIG. 1, Climbazole, is placed in a shampoo formulation and then diluted 1 part shampoo to 10 parts distilled water. The sample is then shaken in a 2 oz vial for 30 seconds and the resulting lather is spread onto a microscope slide. Once dry, the following sequence of images in row 3 of FIG. 1 is captured. Initially, the Climbazole in the shampoo exhibited relatively small levels of autofluorescence when excited with 470 nm light. Upon actinic irradiation, the initial autofluorescence is a strong white fluorescence that quickly turns purple and over time fades to a soft grey tone. Removing the UV irradiation and re-exciting Climbazole with 470 nm light (a second radiation source) shows an increase of fluorescence that gradually fades with continued irradiation. It appears that Climbazole has recrystallized into solid particles.

The scalp care agent may be soluble or in particulate form in the carrier. The scalp care agents can be selected from the group consisting of: pyridinethione salts; azoles, selenium sulphide, particulate sulfur, keratolytic agents such as salicylic acid, and mixtures thereof.

Particulate scalp care agent can be pyridinethione salts, for example salts of 1-hydroxy-2-pyridinethione. Pyridinethione salts are those formed from heavy metals such as zinc, tin, cadmium, magnesium, aluminum and zirconium, generally zinc, typically the zinc salt of 1-hydroxy-2-pyridinethione (known as "zinc pyridinethione" or "ZPT"), Salts formed from other cations, such as sodium, may also be suitable.

The scalp care agent is selected from the group consisting of: coal tar, pine tar, sulfur, charcoal, whitfield' s ointment, castellani' s paint, aluminum chloride, gentian violet, piroctone olamine, ciclopirox olamine, undecylenic acid and its metal salts, potassium permanganate, selenium sulphide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone, and azoles, and mixtures thereof. Further, the scalp care agent may be selected from the group consisting of: itraconazole, ketoconazole, selenium sulphide, coal tar, and mixtures thereof.

The azole scalp care agent can be an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole scalp care agent is a triazole selected from the group consisting of: terconazole, itraconazole, and mixtures thereof.

Additional Examples/Combinations

A. A method for measuring scalp care agents on/in skin or other substrate comprising the following steps: a) selecting a location within the treated area on the skin or other substrate; b) irradiate treated area using an actinic radiation source; and c) measure a resulting fluorescent emission of the scalp care agent or a photoconverted scalp care agent using either the actinic radiation source or a second radiation source to excite the sample.

B. A method for measuring scalp care agents on/in skin or other substrate, according to Paragraph A, wherein the second radiation source provides the wavelengths to excite the sample in step c that range from about 100 to about 700 nm.

C. A method for measuring scalp care agents on/in skin or other substrate, according to Paragraph A-B, wherein the actinic radiation source used in step b or step c provides the wavelengths to excite the sample in step b or step c ranging from about 100 to about 450 nm.

D. A method for measuring scalp care agents on/in skin or other substrate, according to Paragraph A-C, wherein the actinic radiation source used in step b or step c provides the wavelengths to excite the sample in step b or step c ranging from about 280 to about 450 nm.

E. A method for measuring scalp care agents on/in skin or other substrate, according to Paragraph A-D, wherein the actinic radiation source used in step b or step c provides the wavelengths to excite the sample in step b or step c ranging from about 315 to about 450 nm.

F. A method for measuring scalp care agents on/in skin or other substrate, according to Paragraph A-E, wherein in step a, the substrate comprises hair, artificial surrogate, skin, scalp, tape strip, or fabric.

G. A method for measuring scalp care agents on/in skin or other substrate, according to Paragraph A-F, wherein the measurement device is a camera or spectrophotometer.

H. A method for measuring scalp care agents on/in skin or other substrate, according to Paragraph A-G, wherein the measurement device has confocal optical capabilities.

I. A method for measuring scalp care agents on/in skin or other substrate, according to Paragraph A-H, wherein the scalp care agent is a solid particle.

J. A method for measuring scalp care agents on/in skin or other substrate, according to Paragraph A-L, wherein the scalp care agent is selected from the group consisting of zinc pyrithione, piroctone olamine, climbazole and mixtures thereof.

K. A method for measuring scalp care agents on/in skin or other substrate, according to Paragraph A-J wherein the scalp care agent is deposited to said skin or substrate using a cosmetic product.

L. A method for measuring scalp care agents on/in skin or other substrate, according to Paragraph A-K, wherein the location within the treated area is located on the scalp of an individual.

M. A method for measuring scalp care agents on/in skin or other substrate, according to Paragraph A-L, wherein the location within the treated area has a diameter range from about 2.5 microns to about 25 cm.

N. A method for measuring scalp care agents on/in skin or other substrate, according to Paragraph A-M, wherein the location within the treated area has a diameter range of from about 2.5 microns to about 2.5 cm.

O. A method for measuring scalp care agents on/in skin or other substrate, according to Paragraph A-N, wherein the location within the treated area has a diameter range of from about 2.5 microns to about 2.5 mm.

P. A method for measuring scalp care agents on/in skin or other substrate, according to Paragraph A-O, wherein the actinic radiation source is delivered using a light emitting diode, fiber optic probe, or radiation from the sun or any combination thereof.

Q. A method for measuring scalp care agents on/in skin or other substrate, according to Paragraph A-P, wherein the actinic radiation source does not exceed a total dose of about 250 kJ/cm^2.

R. A method for measuring scalp care agents on/in skin or other substrate, according to Paragraph A-Q, wherein the fluorescent emission of the scalp care agent or photoconverted scalp care agent falls in the range of from about 370 to about 800 nm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

In addition to the foregoing, the invention includes, as an additional aspect, all embodiments of the invention narrower in scope in any way than the variations specifically mentioned above. With respect to aspects of the invention described as a genus, all individual species are individually considered separate aspects of the invention. With respect to aspects of the invention described or claimed with "a" or "an," it should be understood that these terms mean "one or more" unless context unambiguously requires a more restricted meaning. With respect to elements described as one or more within a set, it should be understood that all combinations within the set are contemplated. If aspects of the invention are described as "comprising" a feature, embodiments also are contemplated "consisting of" or "consisting essentially of" the feature.

All documents cited in the Detailed Description of the Invention are, in relevant part, incorporated herein by reference; the citation of any document is not to be construed as an admission that it is prior art with respect to the invention. To the extent that any meaning or definition of a term in this document conflicts with any meaning or definition of the same term in a document incorporated by reference, the meaning or definition assigned to that term in this document shall govern.

While particular embodiments of the invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. A method for measuring scalp care agents on/in skin or other substrate comprising the following steps:
    a. selecting a location within the treated area on the skin or other substrate;
    b. irradiate the treated area using an actinic radiation source providing the wavelengths ranging from about 100 to about 450 nm or a functionally equivalent range; and
    c. measure a resulting fluorescent emission of the scalp care agent or a photoconverted scalp care agent using either the actinic radiation source or a second radiation source to excite the sample and wherein the scalp care agent is deposited to the skin or substrate using a cosmetic formulation.

2. A method according to claim 1, wherein the second radiation source provides the wavelengths to excite the sample in step c that range from about 100 to about 700 nm.

3. A method according to claim 1 wherein the actinic radiation source used in step c provides the wavelengths to excite the sample in step c ranging from about 100 to about 450 nm.

4. A method according to claim 1 wherein the actinic radiation source used in step b or step c provides the wavelengths to excite the sample in step b or step c ranging from about 280 to about 450 nm.

5. A method according to claim 1 wherein the actinic radiation source used in step b or step c provides the wavelengths to excite the sample in step b or step c ranging from about 315 to about 450 nm.

6. A method according to claim 1 wherein in step a, the substrate comprises hair, artificial surrogate, skin, scalp, tape strip, or fabric.

7. A method according to claim 1, wherein the measurement device is a camera or spectrophotometer.

8. A method according to claim 1, wherein the measurement device has confocal optical capabilities.

9. A method according to claim 1, wherein the scalp care agent is a solid particle.

10. A method according to claim 1 wherein the scalp care agent is selected from the group consisting of zinc pyrithione, piroctone olamine, climbazole and mixtures thereof.

11. A method according to claim 1, wherein the location within the treated area is located on the scalp of an individual.

12. A method according to claim 1, wherein the location within the treated area has a diameter range from about 2.5 microns to about 25 cm.

13. A method according to claim 1, wherein the location within the treated area has a diameter range of from about 2.5 microns to about 2.5 cm.

14. A method according to claim 1, wherein the location within the treated area has a diameter range of from about 2.5 microns to about 2.5 mm.

15. A method according to claim 1, wherein the actinic radiation source is delivered using a light emitting diode, fiber optic probe, or radiation from the sun or any combination thereof.

16. A method according to claim 1, wherein the actinic radiation source does not exceed a total dose of about 250 kJ/cm^2.

17. A method according to claim 1, wherein the fluorescent emission of the scalp care agent or photo-converted scalp care agent falls in the range of from about 370 to about 800 nm.

* * * * *